(12) United States Patent
Fox et al.

(10) Patent No.: US 9,002,083 B2
(45) Date of Patent: Apr. 7, 2015

(54) SYSTEM, METHOD, AND SOFTWARE FOR OPTICAL DEVICE RECOGNITION ASSOCIATION

(71) Applicant: Covidien LP, Mansfield, MA (US)

(72) Inventors: David Fox, Longmont, CO (US); Robert T. Boyer, Longmont, CO (US); William A. Jordan, II, Westminster, CO (US)

(73) Assignee: Covidien LP, Mansfield, MA (US)

( * ) Notice: Subject to any disclaimer, the term of this patent is extended or adjusted under 35 U.S.C. 154(b) by 87 days.

(21) Appl. No.: 13/768,382

(22) Filed: Feb. 15, 2013

(65) Prior Publication Data

US 2014/0233788 A1 Aug. 21, 2014

(51) Int. Cl.
*G06K 9/00* (2006.01)
*G06K 9/62* (2006.01)
*G06K 9/64* (2006.01)

(52) U.S. Cl.
CPC ........................................ *G06K 9/64* (2013.01)

(58) Field of Classification Search
None
See application file for complete search history.

(56) References Cited

U.S. PATENT DOCUMENTS

| 5,953,452 | A | * | 9/1999 | Boone et al. ................. 382/199 |
| 8,292,807 | B2 | | 10/2012 | Perkins et al. |
| 8,471,899 | B2 | * | 6/2013 | Johnson .......................... 348/77 |
| 8,675,059 | B2 | * | 3/2014 | Johnson et al. ................. 348/77 |
| 8,676,603 | B2 | * | 3/2014 | Johnson .............................. 705/2 |
| 2011/0064283 | A1 | | 3/2011 | Hodson et al. |
| 2011/0305376 | A1 | * | 12/2011 | Neff ............................... 382/128 |
| 2012/0218404 | A1 | * | 8/2012 | Buxton et al. ................. 348/121 |
| 2012/0278103 | A1 | | 11/2012 | Homchowdhury et al. |
| 2012/0321189 | A1 | | 12/2012 | Amir et al. |
| 2012/0330646 | A1 | | 12/2012 | Andrade et al. |
| 2012/0330680 | A1 | | 12/2012 | O'Larte |
| 2013/0339039 | A1 | * | 12/2013 | Roman et al. ..................... 705/2 |
| 2014/0098209 | A1 | * | 4/2014 | Neff ................................ 348/77 |

FOREIGN PATENT DOCUMENTS

WO WO 2004/017831 3/2004

* cited by examiner

*Primary Examiner* — Anand Bhatnagar
*Assistant Examiner* — Soo Park
(74) *Attorney, Agent, or Firm* — Carter, DeLuca, Farrell & Schmidt, LLP (57) ABSTRACT

A system including an image capturing unit configured to capture an image of at least one medical device monitoring a patient, a database including images of a plurality of medical devices, where each image corresponds to a particular medical device, and a data collection server configured to receive the at least one image, receive patient identification data corresponding to the patient, and identify the medical device in the image by comparing the received image with the images stored in the database and matching the received image with the images stored in the database.

15 Claims, 7 Drawing Sheets

SYSTEM, METHOD, AND SOFTWARE FOR OPTICAL DEVICE RECOGNITION ASSOCIATION

TECHNICAL FIELD

The present disclosure relates generally to optical device recognition association, and more particularly to a system, method, and software for optical device recognition association.

BACKGROUND

When monitoring a patient, a medical device may collect and display information about that patient. The medical devices may collect information through one or more of a variety of ways, such as a patient interface that measures a physiological condition, or a user interface that collects information input by a user. The collected information may then be received by a data collection server for processing.

SUMMARY

Aspects of the present disclosure are directed to a system, method, and computer readable recording medium capable of identifying at least one medical device and associating the medical device(s) with a patient by performing the steps of receiving an image which includes at least one medical device in the image, receiving identification data of a patient, identifying the medical device or devices in the image received, and associating the identified medical device with the patient.

By associating the medical devices with the patient, the patient parameters that are captured by the medical device may be stored in a storage unit and processed for review by a clinician for diagnosis or other uses.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

Despite the concept of a networked world where every device is able to talk to every other device, and data transferred between the devices is identified as coming from a particular source, the reality is that most medical facilities have large numbers of legacy devices where such network connectivity is not possible. As a result, the data produced by a particular device must be retrieved manually and thereafter entered into a database for subsequent review and analysis by a clinician. Moreover, though networked (i.e., able to communicate over a medical facility network), many legacy devices do not provide sufficient identification data such that the identity (e.g., serial number, inventory ID, device type, etc.) of a medial device being used by a particular patient can be readily ascertained from the data the medical device produces. Still further, in view of the manual entry of patient identification, patient data, patient parameters being monitored, and other data, occasionally even fully networked devices can be improperly assigned resulting in the patient parameter data being associated with either an improper device or a different patient. The present disclosure incorporates the use of captured images to identify at least one medical device and associate the medical device(s) with a patient for patient monitoring and other uses. By associating the medical devices with the particular patients, the patient parameters captured by the medical devices may be processed, stored, and reviewed by clinicians for diagnoses and patient monitoring, as well as used to confirm the data being provided directly to a database via a network connection.

Figure 1:
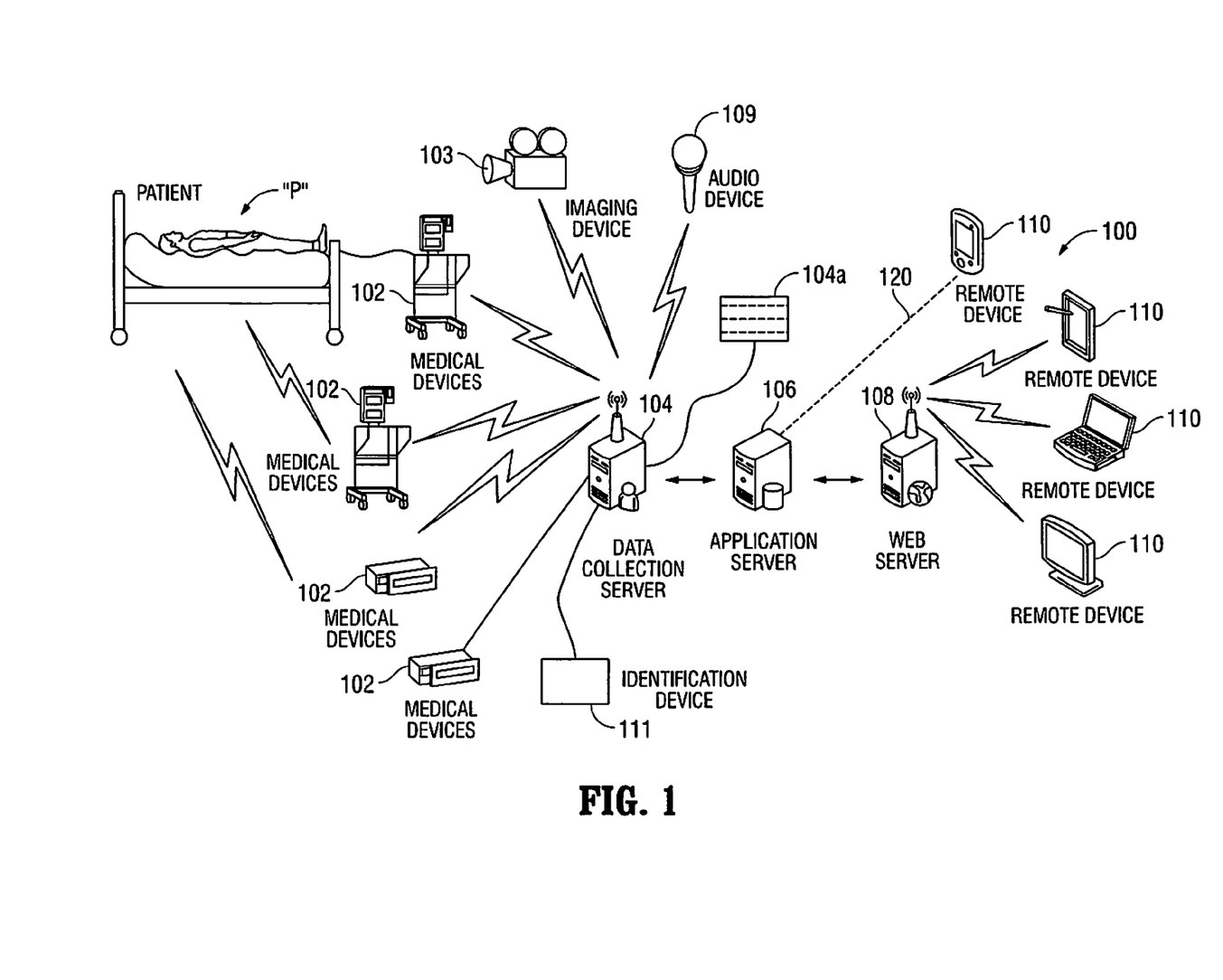
FIG. 1 illustrates an example system for identifying and associating at least one medical device with a patient, according to certain embodiments of the present disclosure.

FIG. 1 illustrates an example system 100 for identifying and associating at least one medical device 102 with a patient, according to certain embodiments of the present disclosure. System 100 includes one or more medical devices 102, an imaging device 103, a data collection server 104, an application server 106, a web server 108, and one or more remote devices 110. System 100 may further include an audio device 109 and an identification device 111.

Although this particular implementation of system 100 is illustrated and primarily described, the present disclosure contemplates any suitable medical implementation of system 100 according to particular needs of the institution or facility. In particular, it is envisioned that system 100 may include some or all of the components described herein. Moreover, although each of the components of system 100 are illustrated and described as separate units, it is understood that any of the components of system 100 may be combined with another component as a single component. For example, although imaging device 103 is shown and described as a separate component from audio device 109 it is envisioned that imaging device 103 may include an the audio device 109. Additionally, although each of the components of system 100 are shown and described as being configured to perform particular functions, it is appreciated that any of the components of system 100 described may be capable of performing any of the functions of the other components described herein.

Medical devices 102, imaging device 103, and/or audio device 109 are used to either generate or capture patient data, such as and without limitation, data relating to the identity of the patient "P," physiological parameters of the patient (also referred to herein as patient parameters), and image or audio data of the patient. System 100 collects the data and stores it, for example on server 104. The system 100 uses one or more of servers 104, 106, and 108 to processes the data and, using various protocols and software, transforms the data such that it can be readily accessed and analyzed via one or more graphic user interfaces (GUI), including some that might be viewed on a remote devices 110. In particular, in one embodiment, prior to presenting the data on a GUI of a remote device 110, the data is processed and analyzed by one or more of the servers 104, 106, and/or 108.

As noted above, system 100 includes one or more medical devices 102. In certain embodiments, the medical devices 102 generate patient data. Patient data may include any patient identifiers, patient parameters, medical history, clinician notes, alarm thresholds, alarm events, device settings, measurements of values indicating physiological conditions such as oxygen saturation levels, pulse rates, heart rates, other vital signs, and any other data input to or output from medical devices 102. Additionally, medical devices 102 display the patient data on a display of the medical device 102 or another display, such as and without limitation a central computing unit or any of remote devices 110. Medical devices 102 may be any devices that are used for monitoring, tracking or treating patients. For example, medical devices 102 may include a ventilator connected to a patient to deliver respiration therapy, a pulse oximeter that monitors the oxygen saturation of a patient's blood, a device for tracking a patient within a hospital with or without monitoring a physiological condition, as well as other medical devices known to those of skill in the art. Additionally, each medical device 102 may take on a particular and distinct appearance which may be utilized in order to differentiate between medical devices 102 and identify each particular medical device 102.

Continuing with reference to FIG. 1, each medical device 102 is connected to data collection server 104, which stores the patient data in a database 104a. In addition to storing patient data, database 104a stores data relating to identified medical devices 102 which are associated with the patient. Application server 106 retrieves and processes the patient data from the database 104a. A web server 108 may be employed to publish the patient data processed by the application server 106, such that it is viewable on a GUI of a remote device 110, thereby enabling clinicians using the remote device 110 to view and analyze the patient data.

Medical devices 102, imaging device 103, and/or audio device 109 are communicatively coupled to data collection server 104 via a network such as a LAN, WAN, or WiLAN employing one or more network communication protocols. In certain embodiments, medical devices 102, imaging device 103, and/or audio device 109 may also be communicatively coupled to the application server 106, web server 108, and remote devices 110.

Continuing with reference to FIG. 1, data collection server 104, application server 106, and web server 108 each include one or more electronic computing devices operable to receive, transmit, process, and store data associated with system 100. Data collection server 104 maps received patient data, images, and medical devices 102 to match internal fields in a database 104a, according to certain embodiments. The stored patient data in the database 104a is accessed by application server 106. Data collection server 104, application server 106, and/or web server 108 use any suitable operating system, as would be understood by those of skill in the art.

According to one embodiment, application server 106 runs one or more applications through which the data collected by the data collection server 104 can be processed and made presentable to a user. A web server 108 creates a data service that publishes a conventional web services platform, which receives data from application server 106, transmits data to remote devices 110, and receives data from remote devices 110 for distribution back to the application server 106 and the data collection server 104. For example, web server 108 may receive data from application server 106 and transmit data, upon request to remote devices 110.

Although FIG. 1 depicts separate devices for data collection server 104, application server 106, and web server 108, it will be readily apparent that the functions of these devices may be combined into just two servers or even a single device that receives patient data from medical devices 102, imaging device 103, and/or audio device 109, and processes the patient data. It will also be understood that the functions may be allocated differently than shown, with application server 106 additionally performing the functions of web server 108 or the functions of data collection server 104.

Figure 2:
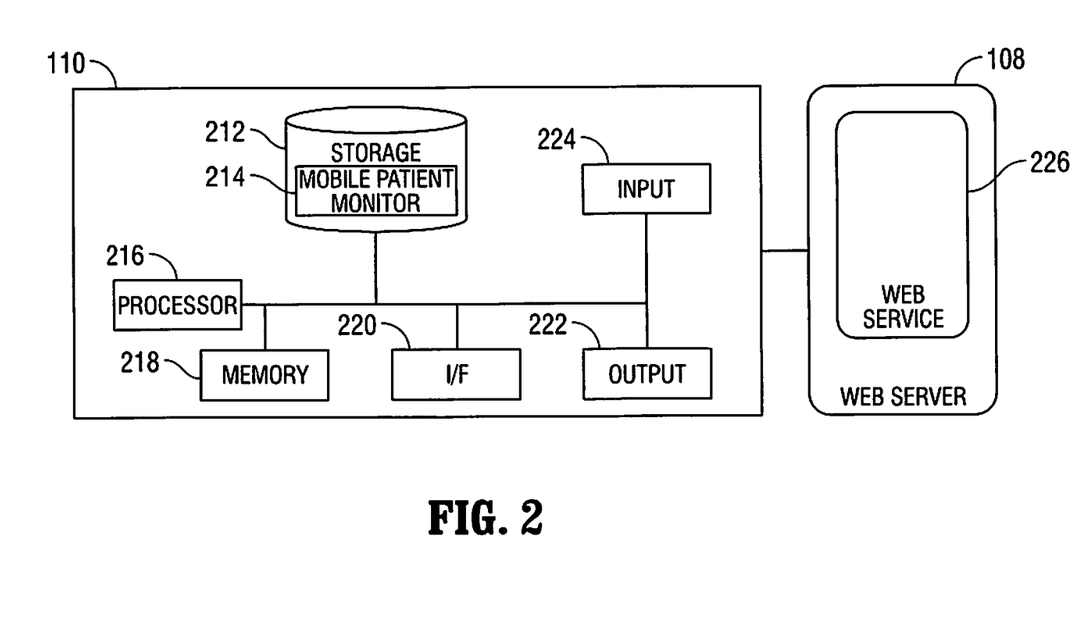
FIG. 2 is a schematic illustration of an example remote device of the system in FIG. 1, according to certain embodiments of the present disclosure.

FIG. 2 illustrates an example remote device 110 of the system 100 in FIG. 1, according to certain embodiments of the present disclosure. Remote device 110 is communicatively coupled with a web server 108 having a web service 226 capability. In certain embodiments, remote device 110 includes a storage device 212 and a mobile patient monitor 214 stored on the storage device 212. The remote device 110 further includes a processor 216, a memory 218, a communication interface (I/F) 220, an output device 222, and an input device 224, which are described in further detail below. Although this particular implementation of remote device 110 is illustrated and primarily described, the present disclosure contemplates any suitable implementation of remote device 110 according to particular needs.

Continuing with reference to FIG. 2, storage device 212 is similar to database 104a and includes any suitable device operable for storing data and instructions. Storage device 212 includes, for example, Random Access Memory (RAM) or Read Only Memory (ROM), EEPROM, a magnetic disk, flash memory, optical disk, or other suitable data storage device.

Mobile patient monitor 214 includes any suitable logic embodied in computer-readable media, that when executed is operable to enable a user to communicate with web service 226 on web server 108 to view and manipulate data, including patient data and perform any other operations in communication with data collection server 104.

Processor 216 includes any suitable device operable to execute instructions and manipulate data to perform operations for mobile patient monitor 214, for example, any type of central processing unit (CPU). Memory 218 includes any computer memory (for example, Random Access Memory (RAM) or Read Only Memory (ROM)), mass storage media (for example, a hard disk), removable storage media (for example, a Compact Disk (CD), a Digital Video Disk (DVD), or USB Flash Drive), database and/or network storage (for example, a server). Memory 218 may comprise any other computer-readable tangible medium, or a combination of any of the preceding. I/F 220 includes any suitable device operable to receive input for mobile patient monitor 214, send output from mobile patient monitor 214, perform suitable processing of the input or output or both, communicate to other devices, or any combination of the preceding, for example appropriate hardware (modem, network interface card, etc.) and software, including protocol conversion and data processing capabilities, to communicate through a LAN, WAN, or other communication system that allows mobile patient monitor 214 to communicate to other devices.

Output device 222 includes any suitable device operable for displaying information to a user, for example, a touch screen, a video display, a printer, a plotter, or other suitable output device. Input device 224 includes any suitable device operable to input, select, and/or manipulate various data and information, for example, a touch screen, a keyboard, mouse, graphics tablet, joystick, light pen, microphone, scanner, or other suitable input device, which may be used for example to input patient identification information to be transmitted to data collection server 104 for processing.

As noted above, system 100 includes one or more imaging devices 103, which generates images that are to be associated with patient data. In particular, the images are used to identify medical devices 102 included in the image, retrieve patient data displayed on the medical devices 102, and associate the medical devices 102 with a particular patient. Image data may include a single image, multiple images, and/or video of a patient and the medical devices 102 monitoring the patient that is captured and then stored in the database 104a. The imaging device 103 is capable of pan, tilt, and zoom movements. The imaging device 103 may be driven in its pan, tilt and zoom movements by input from a user, as is known in the art, either from a remote station on the system 100 network, or from a remote device 110. Additionally, or alternatively, the imaging device 103 may include auto-tracking abilities for panning, tilting, and zooming based on movement of the subject, e.g. the patient, and/or the medical devices 102. Still further, it is contemplated that the imaging device 103 need not be stationary but rather can move in three dimension prior to any pan, tilt, or zoom, thus achieving six degrees of freedom (6-DOF). In this manner, the imaging device 103 can ensure that all of the medical devices 102 being used to monitor a patient may be included in the image(s) captured by imaging device 103. Imaging device 102a may be configured to detect the movement of medical device 102, for example when medical devices 102 are moved by a clinician, nurse, or patient, such that when a medical device is being removed, replaced, or added a new image may be acquired by imaging device 103. In an embodiment, imaging device 103 is configured to scan the entire room, and based on image analysis, zoom into the individual medical devices 102 when they are detected. Additionally, imaging device 103 may be programmed in advance with data corresponding to the layout of a room and location of medical devices 102 in the room, such that the imaging device 103 could traverse and zoom to each of the preprogrammed specified points.

Imaging device 103 includes, without limitation, one or more digital charge-coupled devices (CCD), complementary metal-oxide-semiconductor (CMOS) active pixel sensor, or combinations/hybrids of the two, whether for capturing visible or infrared spectrum light, as well as other image sensors known to those of skill in the art.

Imaging device 103 is configured to capture identification data of the patient "P" and/or the medical devices 102 being used to monitor or treat patient "P," deliver the identification data to the data collection server 104 for further processing and to associate the particular medical devices 102 with the particular patient "P" being monitored by the medical device 102. For example, and without limitation, the medical devices 102 may include bar codes which can be scanned by imaging device 103, and may include facial recognition capabilities to identify the patient "P." The system 100 then associates the specific medical devices 102 with the particular patient "P" being monitored, and analyzes the patient parameters displayed on the medical devices 102. If the medical devices 102 are ever changed, or used for a different patient, or if new medical devices 102 are used for the same patient "P," then the imaging device 103 captures a new image of the new medical device 102 such that the data collection server 104 can update the entries in an appropriate database in data collection server 104 associating medical devices 102 with the patient "P."

One embodiment of the present disclosure is a system 100 configured to identify the medical devices 102 and associate the identified medical device 102 with the particular patient "P" being monitored using imaging device 103. A further embodiment of the present disclosure employs system 100 to read, or otherwise extract, and store the patient data from each medical device 102 from a captured image.

Figure 3A:
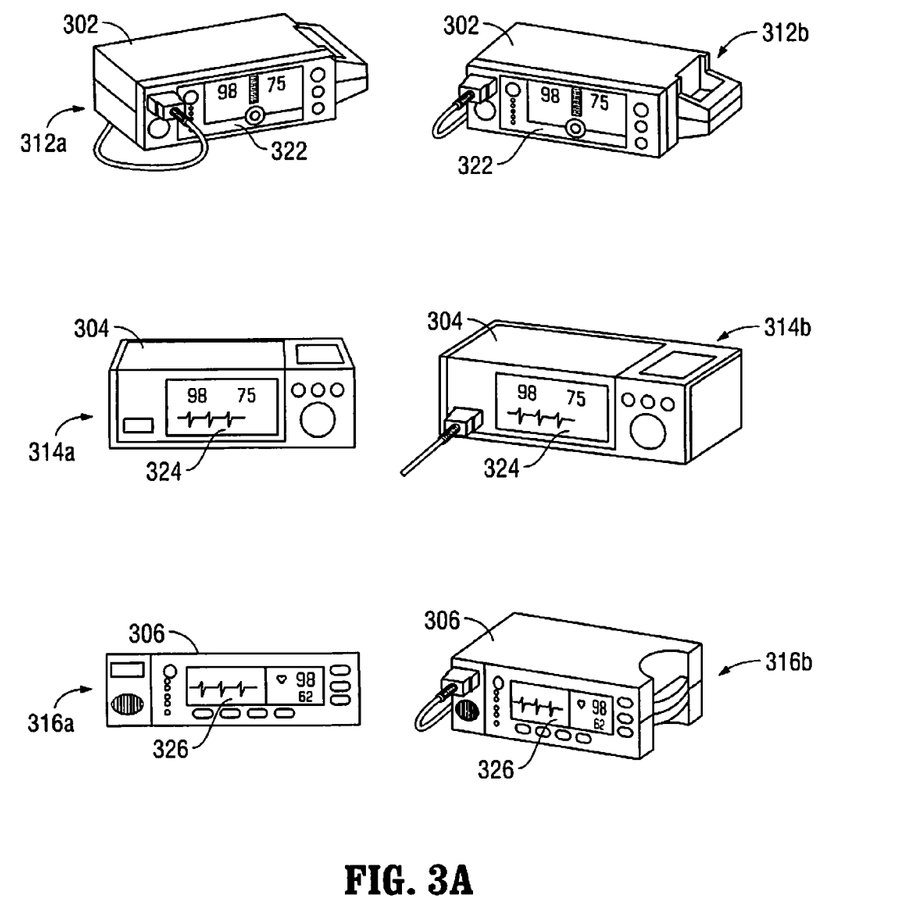
FIG. 3A is an illustration showing images of multiple medical devices from multiple perspectives stored in a database of the system of FIG. 1, according to certain embodiments of the present disclosure.
Figure 3B:
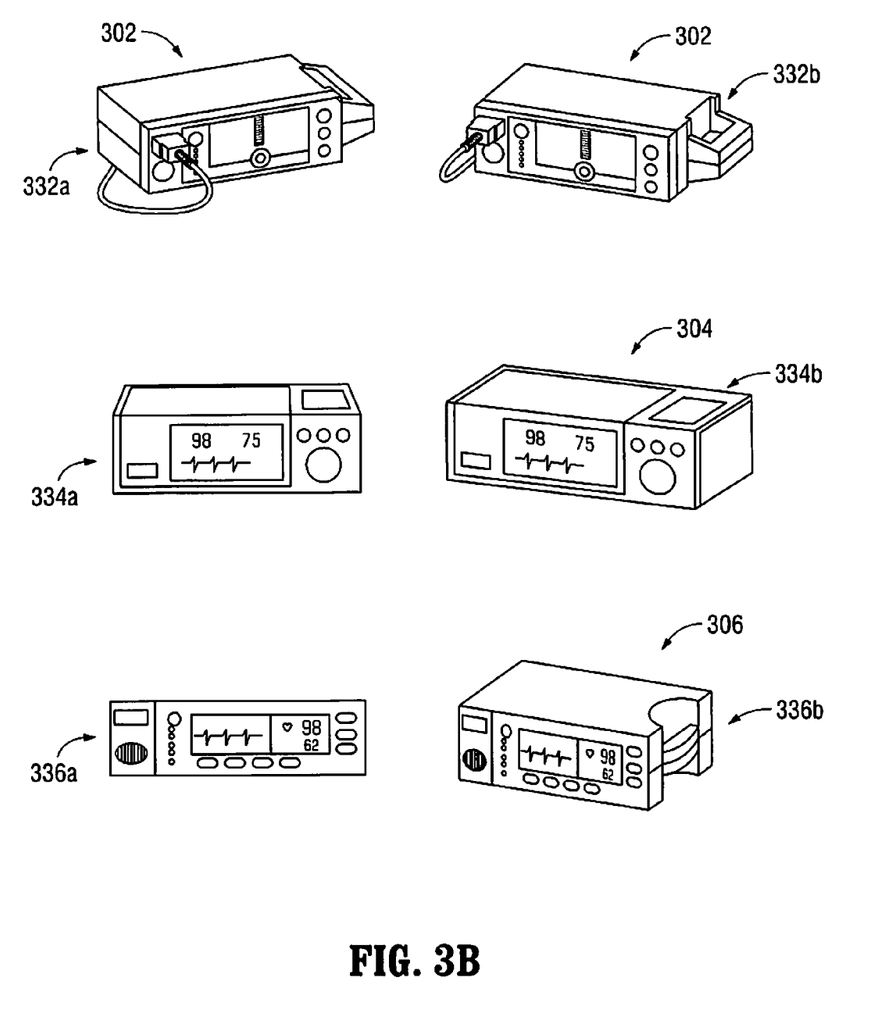
FIG. 3B is a an illustration of the medical devices of FIG. 3A in a wireframe image form, according to certain embodiments of the present disclosure.

FIGS. 3A-3B illustrate a series of exemplary images of medical devices 102 which are stored in database 104a. It will be appreciated that the forms shown in FIGS. 3A-3B do not necessarily correspond to any currently marketed medical device, but are depicted using well known geometric shapes to more clearly denote the different medical devices.

FIG. 3A depicts a series of medical devices 302, 304, 306, which are similar to, and examples of, medical devices 102 described above. One image or a series of images of each of the medical devices 302, 304, 306 are stored in database 104a. In an embodiment, the series of images for each of medical devices 302, 304, 306 includes a 360 degree view of the medical device. In other words, database 104 may include an image from every angle of each of medical devices 302, 304, and 306. As illustrated in FIG. 3A, two images for each of medical devices 302, 304, 306 are stored in database 104a. In particular, two images for medical device 302 are stored in database 104a, including the first image 312a, which is a first perspective view of medical device 302, and the second image 312b, which is a different perspective view of medical device 302. Similarly, two images for medical devices 304 and 306 are also stored in database 104a, including 314a, and 314b, and 316a, and 316b, respectively. Each of images 312a, 312b, 314a, 314b, 316a, 316b will be used by system 100 to identify one or more medical devices 102 captured in an image. Additionally, each of the medical devices 302, 304, 306 include respective displays 322, 324, 326 which displays the patient parameters at the time the image was captured.

FIG. 3B depicts additional or alternative images that may be stored in database 104a. In particular, FIG. 3B illustrates wireframe images of the medical devices 302, 304, 306 of FIG. 3A which may also be used to identify the particular medical device 102 using image analysis. In particular, two images for medical device 302 are stored in database 104a, including a first wireframe image 332a, which is a wireframe image of medical device 302 from a first perspective, and second wireframe image 332b, which is a wireframe image of 302 from a different perspective from the first image. The use of wireframes (FIG. 3B) rather than entire images (FIG. 3A) helps to reduce the volume of image processing necessary to compare a newly captured image of a medical device 102 to those medical devices 302, 304, 306 stored in database 104a. The wireframes are formed by identifying hard edges and seams from an image of the medical device 302, 304, 306, each of these edges and seams receives a line and the remainder is removed from the image. Thus, while it is possible to compare an instant image (FIG. 3A) to one stored in, for example, database 104a for identification purposes, the comparison of an instant image (FIG. 3A) to a wireframe (FIG. 3B) allows for reductions in processing requirements, and also allows easier use of image manipulation techniques, discussed below, to be employed when the instant image is not a perfect match for an existing wireframe.

The images 312a, 312b, 314a, 314b, 316a, 316b and the wireframe images 332a, 332b, 334a, 334b, 336a, 336b of each medical devices 302, 304, 306 are stored in the database 104a. Database 104a includes stored data related to all of the medical devices 102 that used for monitoring or treating patients, which includes images of the medical devices 102. The images or wireframes images of medical devices 102 stored in database 104a may be preselected from a larger database of images and wireframes and limited to just devices currently owned by a medical facility, they may be a standard grouping of images generally employed by a particular type of medical facility, they may be images captured locally by hospital staff to directly correlate to the devices owned by the medical facility, or other combinations of images or wireframes as deemed necessary to facilitate the methods described herein. The stored images or wireframes of the medical devices 102 may be from several viewpoints or views, each of which is intended to help distinguish a particular medical devices 102. As described above, in a particular embodiment, database 104a stores an image for every possible perspective view of every medical device 102.

In additional embodiments, database 104a includes descriptive information of each medical device 102 which may be used for identifying the medical devices 102 captured in the image. For example, database 104a may include information relating to the size, shape, color, etc. of each of the medical devices 102 such that these additional descriptors may be utilized to identify, or assist in identifying, the particular medical devices 102 in the images.

Figure 4:
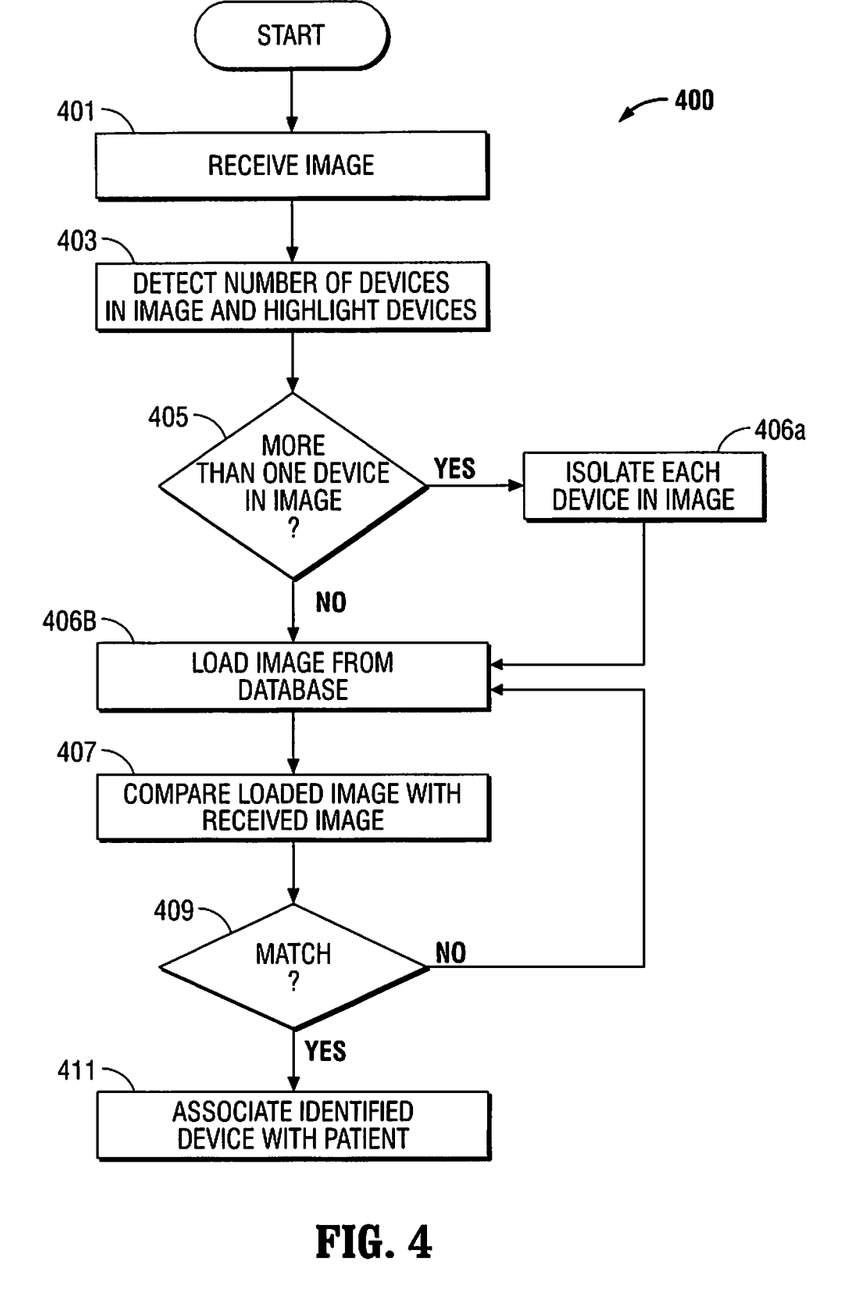
FIG. 4 is a flow chart depicting a method for identifying at least one medical device and associating the identified medical device with a patient, according to certain embodiments of the present disclosure.

Turning now to FIG. 4, a method for identifying at least one medical device 102 and associating the at least one medical device 102 with a patient that the medical device 102 is monitoring or treating is shown as method 400. It is envisioned that although method 400, and any of the other methods described herein, are illustrated and described as including particular steps and are described as in a particular order, method 400, and the other methods illustrated and described herein, may include some or all of the steps described and may be arranged in any order not specifically described.

Beginning with step 401 of method 400, an image is received by data collection server 104. The image received by data collection server is an image captured by imaging device 103 which includes the patient P and one or more medical devices 102 which are to be identified and associated with the patient in the subsequent steps. The medical devices 102 included in the image are the medical devices 102 that are being used or will be used to monitor or treat the patient or otherwise collect patient data. The medical devices 102 captured in the image may include any of medical devices 302, 304, 306 (FIGS. 3A-3B) and any other medical device 102 of which an image is stored in database 104a.

In step 403, data collection server 104, or another component of system 100, analyzes the received image to detect the number of devices included in the image and highlights the medical devices 102 present. In particular embodiments, step 403 further includes utilizing the imaging device's 103 pan, zoom, and tilt capabilities (or 6-DOF capabilities) to change the perspective view of the medical device(s) 102 detected in the image, or refine portions of the image captured. It is envisioned that some patients will be monitored by more than one medical device 102. Thus, at step 403, data collection server 104 highlights the presence medical devices 102 included in the image received in step 401. As shown in step 405, if more than one medical device 102 is detected in the image, then method 400 proceeds to step 406a. Alternatively, if only one medical device 102 is detected in the image, then method 400 proceeds to step 406b. When more than one medical device 102 is detected in step 405 (YES in step 405), method 400 will perform the steps that follow for each image of each medical device 102 that is isolated in step 406a, so that each of the medical devices 102 present in the image received in step 401 will be identified individually.

Additionally, at step 403, data collection server 104 may modify the image received in step 401 if necessary. In particular, the modification may include rotating, resizing, stretching, or skewing the image received in step 401, or portions of the image received, in order to achieve a better perspective view or angle of the medical device 102, or a better zoom of the medical device(s) 102 included in the image. Additionally, or alternatively, it is envisioned that the image captured in step 401 may already include a desired view of each the medical devices 102, and as such, no modification would be necessary. For example, in some applications of the embodiments, the image may include the medical device 102 arranged in a proper zoom and perspective that can be easily matched with an image stored in the database 104a. In one embodiment, the modification include processing the image received in step 401 to produce a wireframe image of the medical device(s) 102 included in the image. In such an embodiment the comparison step 409 discussed below is of the wireframe of the modified received image to wireframes images (FIG. 3B) stored in the database 104a. Additionally, in an embodiment, the imaging device 103 may be controlled to capture new images which include a new angle, tilt, zoom, or perspective of the medical device(s) 102 detected in the previous image captured.

If two or more medical devices 102 are determined to be present in an image (YES in step 405), in step 406a, data collection server 104 modifies the captured image to create a series of images isolating each medical device 102 so that each medical device 102 can be individually identified in the steps to follow. In other words, the series of images comprise one image for each medical device 102 present in the image received in step 401 and each of the series of images will be individually subject to step 406b, 407, 409, and 411 to follow. Additionally, each of the isolated images from step 406a may also undergo the modifications described above to achieve a different perspective and/or zoom of the medical device 102 included in the image.

Subsequent to isolating, highlighting, and/or modifying the image of the medical devices 102 received from step 401, the data collection server 104 loads a new image from the database 104a, in step 406b. In this regard, data collection server 104 is configured to cycle through each of the images of medical devices 102 that are stored in database 104a until a match between the received image from step 401 (or one of the isolated images from step 406a) is found. As described above, the images stored in the database 104a include one or multiple images of a plurality of medical devices 102 (FIG. 3A), and may further include the wireframe images of the medical devices 102 (FIG. 3B).

In step 407, data collection server 104 compares the image received in step 401 (or the series of images with isolated medical devices 102), which may or may not have been modified, with the image loaded from the database in step 406b. At this point, data collection server 104 may have modified the received image in some manner so that the medical devices 102 are isolated, modified to a preferred perspective, and/or converted to a wireframe image. Step 407 can be carried out by several means, each of which is described below.

In a first embodiment, in step 407 data collection server 104 compares the image received from step 401 directly with the image loaded from the database 104a, where the image loaded from the database 104a is an image of a medical device 102 from a first perspective, similar to image 312a of medical device 302 (FIG. 3A). In a second embodiment, in step 407, data collection server 104 compares the image received from step 401 with an image loaded from the database 104a, where the image loaded from the database 104a is a wireframe image of a medical device 102 from a first perspective, similar to image 322a of medical device 302 (FIG. 3B). In a third embodiment, data collection server 104 modifies the image received from step 401 in such a manner so as to transform the image into a wireframe image. In such an embodiment, in step 407, data collection server 104 compares the transformed image (now wireframe) with an image loaded from the database 104a, where the image loaded from the database 104a is a wireframe image of a medical device 102 from a first perspective, similar to image 322a of medical device 302 (FIG. 3B). Irrespective of which means is used for completing step 407, method 400 proceeds to step 409 to determine if a match is found.

In step 409, data collection server determines if the images compared in step 407 are a match. Data collection server uses image matching techniques known in the art to determine if the two compared images are considered match beyond a certain threshold or degree. A match is found for example, by overlaying the images (FIG. 3A) or wireframe images (FIG. 3B) stored in the database 104a on the image of the medical device 102 received in step 401 (which may have been modified). In one embodiment, a match is found when sufficient portions of the image or wireframe image match edges and seams of the medical device to substantially exclude all other options. For example, a threshold may be set that the image must have at least a 75% similarity in order to be considered a match for step 409. In an embodiment, the degree of similarity between the images compared are also provided to the user.

If a match is not found in step 409 (NO in step 409), then method 400 reverts back to step 406b, where the next image stored in database 104a is loaded. The next image stored in the database 104a is an image of the same medical device as the previous image, except from a different perspective. Alternatively, if all of the perspectives of a particular medical device 102 are determined to not match the image received in step 401, then the next image loaded from the database 104a is an image of a different medical device 102. For example, after determining that image 312a (FIG. 3A) is not a match to the received image from step 401, data collection server 104 then loads image 312b (FIG. 3A) from database 104a to determine if the received image is a match with figure 312b. This process is a continuous cycle, where each image is compared until a match beyond a certain degree of certainty, i.e. the threshold set, is found. Once a match is found (YES in step 409), then method 400 proceeds to step 411 where the medical device 102 is identified and thus may be associated with the patient that the medical device 102 is monitoring.

In an alternative embodiment, data collection server 104 causes the received image to be displayed on a user interface of a remote device 110. A clinician or other user may view these images and recognize the particular medical device in the image, and at that point, may identify the medical device 102 being used to monitor the patient, or otherwise associated with the patient. Alternatively, the system 100 may request the user or clinician confirm the identity of a medical device 102 identified by the system 100. In an embodiment, the system 100 may store the user's response to a previously unrecognized medical device 102 and use the response and identification for future identifications of the medical device 102 included in the image.

At any point prior to, or during, method 400, patient identification data may be received by data collection server 104. For example, a clinician may input the patient identification data for the data collection server 104 to receive. It is envisioned that this may be accomplished by scanning a barcode located on a wristband of the patient, where the barcode has been previously attached to the patient to identify the patient within the medical facility. Alternatively, the patient identification information may be received via facial recognition of the patient included in the image captured. For example, system 100 may be configured to identify the patient included in the image captured by the imaging unit in step 401 by comparing the image taken in step 401 with a previously taken image, for example at patient in-processing, which has been stored in database 104a.

In a further embodiment, system 100 utilizes neural network techniques to identify the particular medical devices 102 included in the image received in step 402. In this regard, database 104a may include a collection of images of medical devices 102 from different angles, with different patient data, or no patient data, displayed on the display of the particular medical device 102. This collection of images may be used to train the neural net. In certain embodiments, more images of medical devices 102 are captured in the training process for the purpose of validating that the neural net has learned the correct associations.

Figure 5:
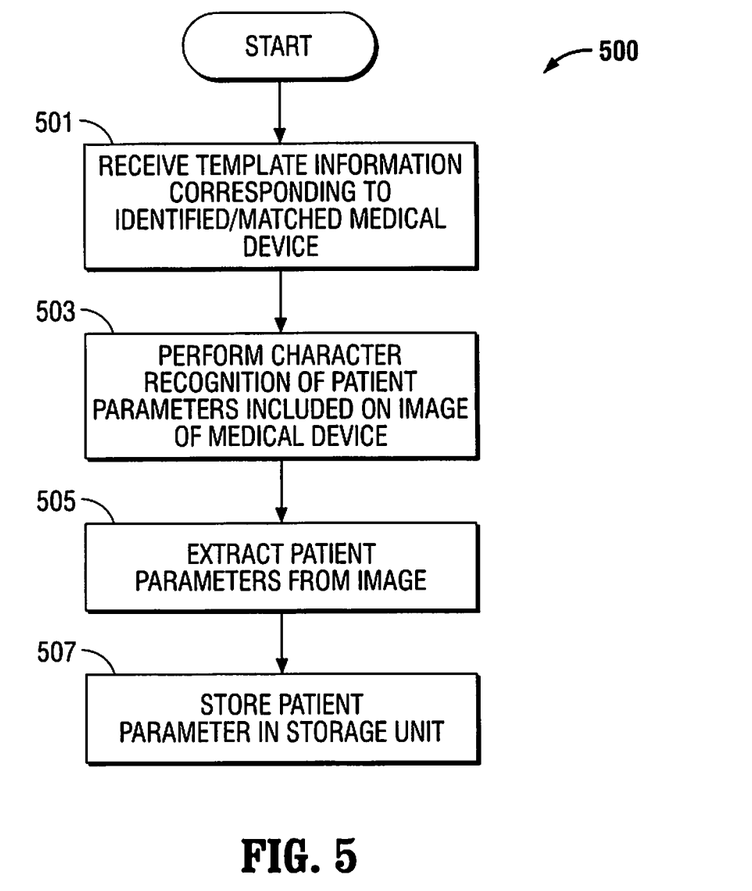
FIG. 5 is a flow chart depicting a method for extracting patient parameters from an image, according to certain embodiments of the present disclosure.

Turning now to FIG. 5, a method for reading and storing patient parameters is illustrated and described as method 500. Database 104a includes a template corresponding to each particular medical device 102. Template information relates to the size and orientation of a display on the medical device 102, as well as identifying the parameters found in each portion of the display. Each of medical devices 302, 304, and 306 correspond to a particular template which is used by system 100 after the specific medical device 302, 304, 306 is identified to extract the patient parameters that are displayed on the display 322, 324, 326 of medical device 302, 304, 306, respectively, from the image captured. The templates include cells which are used for identifying the values present on the front of the respective medical device 102. The templates are used for entering patient parameters, or other patient data, extracted from the images captured, as will be described in further detail below.

Method 500 begins with step 501 were data collection server 104 receives template information corresponding to the medical device 102 identified in method 400. In this manner, method 500 works in conjunction with method 400. At this point, with the corresponding template information received, data collection server 104 is capable of identifying the data included on the images received, and thus may extract the data from the image. Subsequent to completing step 501 and receiving the corresponding template information, method 500 proceeds to step 503.

In step 503, image processing software resident on data collection server 104, performs character recognition of the patient data, i.e. patient parameters, included on the images of the particular identified medical device 102. Using the template received for that particular medical device 102 in step 501, data collection server 104 may then proceed to extract the patient data, i.e. the patient parameters, from the image, and correlate that patient data into proper entries in a patient parameter database 104a. In addition, the templates may provide the data collection server 104 with the necessary information, i.e. instructions, that enable the data collection server 104 to extract, or otherwise analyze the image to extract the data displayed on the display of the medical device 102. Subsequent to completing step 505, method 500 then proceeds to step 507.

With particular reference to step 503, in one embodiment a specific cell corresponding to a particular patient parameter is identified in the image using the template information received. The cell is isolated, and everything that is not in that specific cell is cropped out of the image, such that the particular cell that has been isolated may undergo the character recognition. In another embodiment, the template is in the form of an image and the image of the template is altered to match the perspective of the image of the medical device 102. Once the perspective and size of the two images (the image of the template and the image of the medical device 102) are sufficiently matched, the character recognition is performed. In yet another embodiment, character recognition is performed directly and cell location is managed from a relative perspective. Any of the embodiments described above, and others, may be utilized to determine which portions of the image are associated with the corresponding cells of the template.

In step 507, data collection server 104 stores the patient data, i.e. the patient parameters extracted in step 505 in the database 104*a*. In this way, a non-networked device can have patient parameters that are either monitored or generated based on the treatment offered by the device, automatically collected and stored electronically. Employing such a system eliminates the collection of such data manually and minimizes the opportunity for errors often associated with transposition of such manually collected data.

Yet a further use of such data captured via image analysis as described above, is for the purpose of confirming data received via other methods. As contemplated herein, use of the image data can be used to confirm that a networked device is properly identified as associated with a particular patient, and providing accurate data to the database 104*a*, as will be described in further detail below with reference to FIG. 6.

Figure 6:
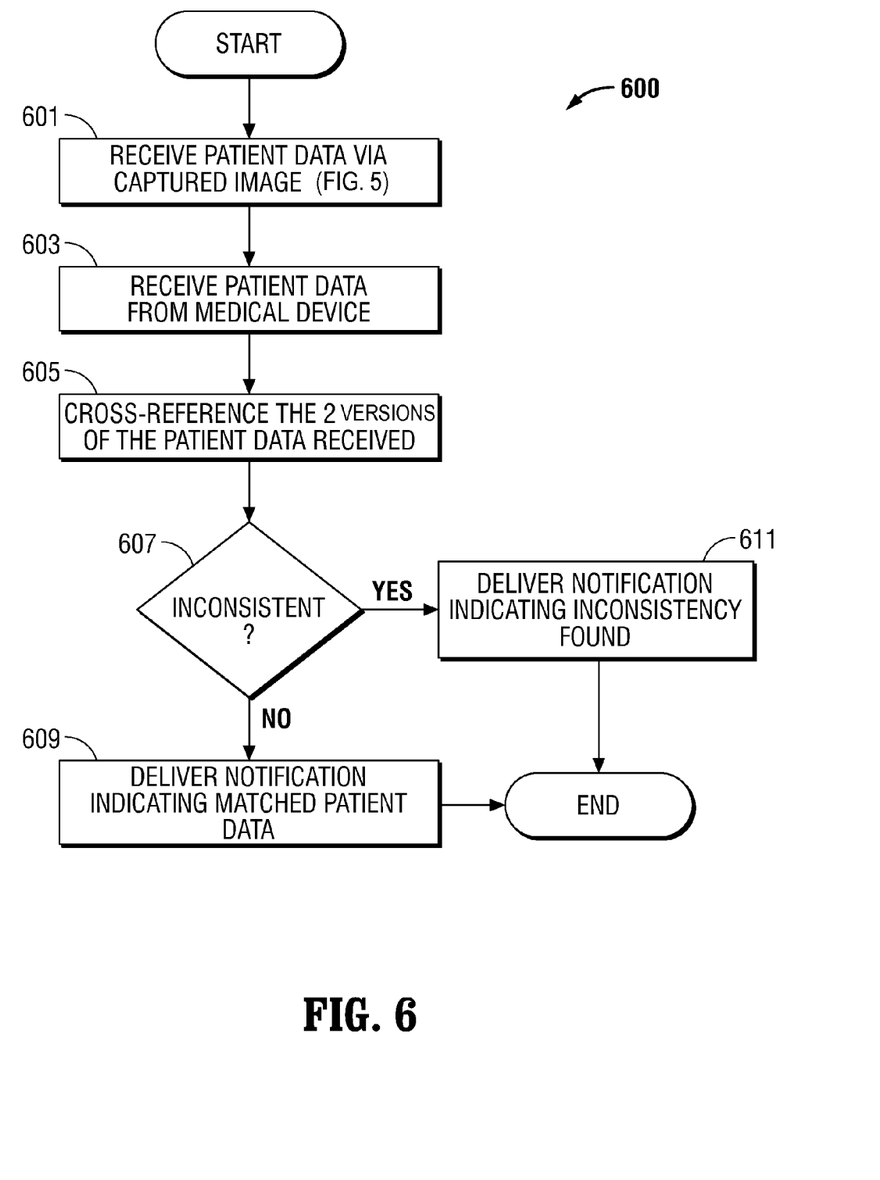
FIG. 6 is a flow chart depicting a method for verifying patient data, according to certain embodiments of the present disclosure.

Turning now to FIG. 6, a method for verifying patient data, e.g. patient parameters, is illustrated and described as method 600. Method 600 begins with step 601 where data collection server 104 receives the patient data, i.e. the patient parameters, via the captured image from method 500 (FIG. 5). Subsequent to receiving the patient data via the captured image in step 601, or concurrent with receiving the data in step 601, data collection server 104 receives patient data directly from the medical device 102, as shown in step 603. As described above, in certain embodiments, each medical device 102 is capable of transmitting patient data, e.g. patient parameters, to the data collection server 104 independent of the patient data being extracted from the image captured by the imaging device 103. Data collection server 104 will thus include two separate and independent versions of patient data, the first version of patient data is the data extracted from the image (step 601), and the second version of the patient data is the data received directly from the medical device 102 (step 603).

In step 605, data collection server 104 cross-references the two versions of patient data received from steps 601 and 603. In particular, as shown in step 607, data collection server 104 compares the two versions for inconsistencies. If inconsistencies are present when comparing the two versions (YES in step 607), then method 600 proceeds to step 611 where a notification is delivered which indicates that an inconsistency between the two versions was found. Alternatively, if inconsistencies are not present (NO in step 607), then method 600 proceeds to step 609 where a notification is delivered which indicates that the two versions are a match, and thus the patient data is verified. In one embodiment the notifications 609, 611 are delivered to the remote device 110 for review by a clinician.

Yet a further aspect of the present disclosure involves the resolution of potential duplicate data sets that might be generated when associating a patient with a device for the first time. According to this method, upon detection of potential duplicates the system alerts a clinician that potential duplicates have been detected. Upon receiving the alert the clinician changes one or more of the settings of the device, by this action the change in setting renders the data output by the device unique and identifies the data between the two potential duplicates allowing for clear identification of the device and proper association with a patient.

Certain embodiments of the present disclosure comprise logic for associating medical devices with a particular patient for uses such as patient monitoring, and may be embodied in at least one tangible, computer-readable medium. For example, when the logic is executed, it may be operable to receive an image of the patient and/or the medical devices configured to monitor the patient, identify each of the medical devices, store the identified device, receive patient identification information, associate the medical device with the patient, and extract patient data from the image of the medical device.

In certain embodiments, the logic for associating the medical devices with the particular patient may be embodied in more than one tangible, computer-readable medium. For example, portions of the logic for patient monitoring and association of medical devices may be embodied in one or more of medical device 102, data collection server 104, application server 106, web server 108, and remote device 110 of system 100 in any manner.

Although the present disclosure describes certain embodiments, various alterations and permutations of the embodiments will be apparent to those skilled in the art. Accordingly, the above description of the embodiments does not constrain this disclosure. Other changes, substitutions, and alterations are possible without departing from the spirit and scope of this disclosure, as defined by the following claims.

What is claimed is:

1. A system comprising:
   an image capturing unit configured to capture at least one image of at least one medical device monitoring a patient, the at least one medical device measuring physiological parameters of the patient and displaying the measured physiological parameters of the patient on a display of the at least one medical device, wherein the measured physiological parameters of the patient are viewable in the at least one captured image;
   a database including images of a plurality of medical devices, wherein each image corresponds to a particular medical device at a particular angle; and
   a data collection server configured to:
   receive the measured physiological parameters from the at least one medical device;
   receive the at least one image;
   receive patient identification data corresponding to the patient;
   detect the at least one medical device in the at least one received image;
   modify the at least one received image to prepare the at least one received image for comparison;
   compare the at least one received image with the images stored in the database and match the at least one received image with at least one of the images stored in the database to identify the particular medical device;
   extract the measured physiological parameters of the patient from the at least one received image; and
   verify the measured physiological parameters of the patient by comparing the measured physiological parameters received from the at least one medical device with the measured physiological parameters extracted from the at least one received image.

2. The system according to claim 1, wherein the data collection server is further configured to select the medical devices in the image, rotating each selected medical device, and scaling each medical device.

3. The system according to claim 1, wherein the data collection server matches the at least one received image with the images stored in the database via neural network techniques.

4. The system according to claim 1, wherein each particular medical device corresponds to a template which includes cells in different locations, and wherein the measured physiological parameters of the patient included in the at least one image are associated with the corresponding cells and stored in the database as patient data.

5. The system according to claim 1, wherein the images stored in the database include wireframe images of each of the plurality of medical devices, and wherein at least a portion of the at least one received image is compared to the wireframe images of each of the plurality of medical devices.

6. The system according to claim 5, wherein at least a portion of the at least one received image is modified into a wireframe image.

7. A method for optical device recognition association, comprising:
   capturing at least one image of at least one medical device monitoring a patient, the at least one medical device measuring physiological parameters of the patient and displaying the measured physiological parameters of the patient on a display of the at least one medical device, wherein the measured physiological parameters of the patient are viewable in the at least one captured image;
   receiving the measured physiological parameters from the at least one medical device;
   receiving the at least one image;
   receiving patient identification data corresponding to the patient;
   detecting the at least one medical device in the image;
   modifying the at least one received image to prepare the at least one received image for comparison;
   comparing the at least one received image with images stored in a database corresponding to particular medical devices and match the at least one received image with at least one of the images stored in the database to identify the particular medical device;
   extracting the measured physiological parameters of the patient from the at least one received image; and
   verifying the measured physiological parameters of the patient by comparing the measured physiological parameters received from the at least one medical device with the measured physiological parameters extracted from the at least one received image.

8. The method according to claim 7, wherein modifying the at least one received image includes selecting the medical devices in the at least one received image, rotating each selected medical device, and scaling each medical device.

9. The method according to claim 7, further comprising matching the at least one received image with the stored images via neural network techniques.

10. The method according to claim 7, wherein each particular medical device corresponds to a template which includes cells in different locations, and wherein the measured physiological parameters included in the at least one image are associated with the corresponding cells and stored in the database as patient data.

11. The method according to claim 7, wherein the images stored in the database include wireframe images of each medical device, and wherein at least a portion of the at least one received image is compared to the wireframe images of each medical device.

12. The method according to claim 11, further comprising modifying at least a portion of the at least one received image into a wireframe image.

13. A non-transitory computer-readable storage medium storing a program which, when executed by a computer, causes the computer to perform a method for optical device recognition association, comprising:
   capturing at least one image of at least one medical device monitoring a patient, the at least one medical device measuring physiological parameters of the patient and displaying the measured physiological parameters of the patient on a display of the at least one medical device, wherein the measured physiological parameters of the patient are viewable in the at least one captured image;
   receiving the measured physiological parameters from the at least one medical device;
   receiving the at least one image;
   receiving patient identification data corresponding to the patient;
   detecting the at least one medical device in the image;
   modifying the at least one received image to prepare the at least one received image for comparison;
   comparing the at least one received image with images stored in a database corresponding to particular medical devices and match the at least one received image with at least one of the images stored in the database to identify the particular medical device; and
   extracting the measured physiological parameters of the patient from the at least one received image; and
   verifying the measured physiological parameters of the patient by comparing the measured physiological parameters received from the at least one medical device with the measured physiological parameters extracted from the at least one received image.

14. The non-transitory computer-readable storage medium according to claim 13, wherein modifying the at least one received image includes selecting the medical devices in the at least one received image, rotating each selected medical device, and scaling each medical device.

15. The non-transitory computer-readable storage medium according to claim 13, wherein the instructions when executed by the computer further cause the computer to match at least a portion of the at least one received image with the stored images via neural network techniques.

* * * * *